United States Patent
Debnath et al.

(10) Patent No.: US 10,016,044 B2
(45) Date of Patent: Jul. 10, 2018

(54) APPLICATOR HEAD FOR FLUID MATERIAL

(71) Applicant: GlaxoSmithKline (China) Investment Co. Ltd., Bejing (CN)

(72) Inventors: Gautam Debnath, Parsippany, NJ (US); Mingsheng Hu, Shanghai (CN); Nan Ma, Shanghai (CN)

(73) Assignee: GlaxoSmithKline (China) Investment Co. Ltd, Beijing (CN)

(*) Notice: Subject to any disclaimer, the term of this patent is extended or adjusted under 35 U.S.C. 154(b) by 0 days.

(21) Appl. No.: 14/784,673

(22) PCT Filed: Apr. 16, 2014

(86) PCT No.: PCT/IB2014/060762
§ 371 (c)(1),
(2) Date: Oct. 15, 2015

(87) PCT Pub. No.: WO2014/170841
PCT Pub. Date: Oct. 23, 2014

(65) Prior Publication Data
US 2016/0095414 A1 Apr. 7, 2016

(30) Foreign Application Priority Data
Apr. 16, 2013 (CN) .......................... 2013 1 0130818

(51) Int. Cl.
*A47L 13/30* (2006.01)
*A45D 34/04* (2006.01)
(Continued)

(52) U.S. Cl.
CPC .......... *A45D 34/04* (2013.01); *A61M 35/003* (2013.01); *B65D 35/36* (2013.01); *B65D 47/243* (2013.01); *B65D 47/42* (2013.01)

(58) Field of Classification Search
CPC ....... A45D 34/04; B65D 47/243; B65D 47/42
(Continued)

(56) References Cited

U.S. PATENT DOCUMENTS 2,961,679 A * 11/1960 Claypool ............... A45D 40/26
401/266
4,690,304 A * 9/1987 Morel .................... B65D 47/24
222/153.14
(Continued)

FOREIGN PATENT DOCUMENTS

| CN | 1675109 A | 9/2005 |
|---|---|---|
| CN | 200967608 Y | 10/2007 |

(Continued)

OTHER PUBLICATIONS

First Office Action dated Jul. 25, 2014, Chinese counterpart application ZL2013101308180.
(Continued)

*Primary Examiner* — Jennifer C Chiang
(74) *Attorney, Agent, or Firm* — Joshua C. Sanders

(57) ABSTRACT

An applicator head for a fluid material comprising a neck part having a flow conduit for the flow of the fluid material and an outlet part comprising a slideable sleeve externally mounted on the neck part, the neck part incorporating a closure part engages with the outlet opening to close it, and the outlet part has an external applicator surface adapted to apply the fluid material to a user's skin and the outlet opening is an opening through the applicator surface.

13 Claims, 6 Drawing Sheets

(51) Int. Cl.
  *B65D 35/36* (2006.01)
  *B65D 47/24* (2006.01)
  *B65D 47/42* (2006.01)
  *A61M 35/00* (2006.01)

(58) Field of Classification Search
  USPC .............................. 401/263, 265, 266, 270
  See application file for complete search history.

(56) References Cited

U.S. PATENT DOCUMENTS

| | | | |
|---|---|---|---|
| 5,193,928 | A | 3/1993 | Balzer et al. |
| 6,675,812 | B1 | 1/2004 | Wiley |
| 6,739,781 | B2 * | 5/2004 | Maloney ................ B65D 47/42 222/544 |
| 7,374,361 | B1 * | 5/2008 | Kwon .................... A45D 34/04 401/202 |
| 7,988,377 | B2 * | 8/2011 | Zhang ................... A45D 40/24 401/186 |
| 2002/0048481 | A1 | 4/2002 | Gueret |
| 2008/0101850 | A1 * | 5/2008 | Wojcik ................... A45D 34/04 401/265 |

FOREIGN PATENT DOCUMENTS

| | | |
|---|---|---|
| CN | 101415617 A | 4/2009 |
| CN | 2 956 954 A1 | 9/2011 |
| CN | 1344664 A | 4/2012 |
| CN | 202481 503 | 10/2012 |
| CN | 103171819 A | 6/2013 |
| CN | 203186771 | 9/2013 |
| EP | 0 257 426 A2 | 3/1988 |
| EP | 0 303 275 A2 | 2/1989 |
| EP | 0 378 488 A1 | 7/1990 |
| EP | 0 520 939 A1 | 5/1992 |
| EP | 0875465 A1 | 11/1998 |
| EP | 2 003 066 A2 | 12/2008 |
| EP | 2 014 569 A1 | 1/2009 |
| FR | 2 894 566 A1 | 6/2007 |
| WO | WO2003101858 A2 | 12/2003 |

OTHER PUBLICATIONS

EPO Communication dated Nov. 22, 2016, from counterpart application EP14786052.2.
EPO Communication dated Aug. 18, 2017, from counterpart application EP14786052.2.

* cited by examiner

APPLICATOR HEAD FOR FLUID MATERIAL

This application is a 371 of International Application No. PCT/IB2014/060762, filed Apr. 16, 2014, which claims the priority of CN Application No. CN201310130818.0 filed Apr. 16, 2013, which is incorporated herein in its entirety.

This invention relates to applicator heads for applying a fluid material to a user's skin.

In the field of application of fluid materials such as creams to a user's skin, for example for therapeutic or cosmetic purposes, it is known to provide a dispensing container of the fluid with an applicator head having an applicator surface adapted for application of the fluid material to the user's skin. Such applicator heads normally incorporate a conduit for the flow of the fluid material in a flow direction from the dispensing container to a dispensing opening in or adjacent to the application surface. Such applicator heads may be provided integrally with a dispensing container, or connectable with a dispensing container. A typical dispensing container is a squeeze tube of the fluid material with a screw-threaded outlet nozzle.

Closures for dispensing containers are known of the type comprising a neck part with an inner conduit for a fluid material, on which is mounted an outer nozzle part which is slideable between two positions. The nozzle part has an outlet opening and the neck part incorporates a closure plug which closes the outlet opening art so that when the applicator part is in one position the plug closes the outlet opening, and in the other position the outlet opening is open to allow flow of the fluid material. U.S. Pat. No. 2,998,902; U.S. Pat. No. 3,227,332 are typical of such closures.

Such known dispensers are not optimized for application of a fluid material dispensed from the dispensing container onto a user's skin, e.g. a cosmetic or therapeutic cream. It is an object of this invention to provide a closure adapted to apply the fluid to a user's skin.

It is an object of this invention to provide an improved applicator head which provides easier handling and application of fluid materials to a user's skin. Other objectives and advantages of the invention will be apparent from the following description.

According to this invention, an applicator head for a fluid material is provided comprising:

a neck part having a flow conduit for the flow of the fluid material in a flow direction between an inlet end of the conduit and an outlet end of the conduit;

an outlet part comprising a skirt wall descending from an end wall and comprising a sleeve externally mounted on the neck part and being reciprocally sideably moveable on the neck part between a first position and a second position, the outlet part having an outlet opening through which fluid material may flow, the neck part incorporating a closure part which when the outlet part is in the first position is engaged with the outlet opening to close flow of the fluid material from the flow conduit through the outlet opening, and when the outlet part is in the second position is disengaged from the outlet opening to allow flow of the fluid material from the flow conduit through the outlet opening, wherein the outlet part has an external applicator surface adapted to apply the fluid material to a user's skin and the outlet opening is an opening through the applicator surface.

Preferably the applicator head of the invention is connectable, or integrally connected to a container of the fluid material, preferably to the outlet nozzle of a squeeze tube, in a manner such that the fluid material content of the container are in flow communication with the flow conduit.

The neck part is preferably a tubular member with the flow conduit following a linear axis through the neck part. Suitably the neck part is generally cylindrical or has a cylindrical portion on its outer surface upon which the outlet part slides in the cylindrical axis direction. Suitably the part of the neck part adjacent to the inlet end of the conduit, or the inlet end itself of the flow conduit, is provided with connection means such as a screw thread to enable connection to a dispensing container of the fluid material, for example a screw-threaded nozzle of a squeeze tube.

Preferably the skirt wall of the outlet part is a tight sliding fit on the outer surface of the neck part. Preferably the inner profile of the outlet part corresponds closely to the outer profile of the neck part, so as to form a fluid material-tight sliding fit between them.

Preferably the outlet part is reciprocally sideably moveable on the neck part between a first position and a second position which are separated along the flow direction of the fluid material through the flow conduit.

The neck part and the outlet part, e.g. the skirt part, suitably have co-operating end-stop means on their respective outer and inner surfaces which slide relative to each other, provided to limit the distance the outlet part can move between the first and second positions. Such end-stop means may comprise engaging steps and/or ridges. Suitably such engaging steps and/or ridges may also engage to prevent the outlet part from being easily dislodged from the neck part.

The neck part and the outlet part, e.g. the skirt part, may also incorporate co-operating guide parts to guide the outlet part and the neck part in their relative sliding motion. For example such guide parts may comprise one or more co-operating tooth and slot which allow relative motion only in the longitudinal direction of the slot and which restrict or prevent relative rotation of the outlet part and neck part.

Frictional engagement between the outlet part and the neck part, e.g. between the above-mentioned one or more co-operating tooth and slot may help to retain the outlet part in its first (closed) position.

The external applicator surface of the outlet part may be provided by various constructions of the outlet part.

In one construction the external applicator surface comprises an external surface of the end wall and/or the skirt wall of the outlet part, preferably of the end wall.

Such an applicator surface may comprise an external surface of the end wall of a generally flat, preferably gently rounded external shape which extends across a substantial proportion of the widest cross sectional dimension of the outlet part, preferably 60% or more, especially 70% or more. Suitably for user comfort such an external surface and the skirt wall meet with a rounded edge between them. Such an applicator surface may be substantially in a plane perpendicular to the flow direction of the fluid material along the flow conduit, and/or if the applicator head is for connection via its connection means to a dispensing container of the fluid material which is an elongate squeeze tube, to the elongate direction of such a squeeze tube. Alternatively such an applicator surface may be substantially in a plane which is at a non-perpendicular angle to the flow direction and/or the elongate direction of such a squeeze tube. A suitable non-perpendicular angle for such an applicator surface is 60°+/−10° to the flow direction and/or the elongate direction of such a squeeze tube.

Alternatively the applicator surface may be a generally hemispherical or ogival shaped part of the outer surface of the outlet part, with its rotation axis e.g. the spherical radius or ogival axis aligned with the flow direction and/or the elongate direction of a squeeze tube. In such a construction at least part of the applicator surface may face transverse to the flow direction and/or the elongate direction of such a squeeze tube.

The external applicator surface may be smooth. Alternatively the external applicator surface may be roughened, e.g. with surface undulations. Such roughening of the applicator surface can help to spread the fluid material over the user's skin surface. One form of such undulations comprises one or plural surface ridges. For example such plural ridges may be generally circular or oval in plan and may be nested within each other, e.g. such ridges may be concentric. Such nested ridges may be arranged around, e.g. be concentric around, an axis which is aligned with the flow direction and/or the elongate direction of the squeeze tube. Alternatively such ridges may be located on an applicator surface which faces in a direction transverse to the flow direction and/or the elongate direction of the squeeze tube. Another form of undulations comprises localized raised portions of the external applicator surface, for example bumps on the applicator surface.

The outlet opening is suitably an orifice through the outlet part, e.g. through the skirt or end wall, and opening through or adjacent to the external applicator surface and so providing communication between the applicator surface and the interior of the outlet part, and consequently between the applicator surface and the flow conduit when the outlet part is in its second position.

The closure part suitably comprises a plug part which when the outlet part is in the first position fits into the outlet opening to close it, and when the outlet part moves toward the second position becomes removed from the outlet opening. Suitably therefore the plug part has dimensions which correspond closely to those of the outlet opening. Suitably such a plug part extends from the outlet end of the conduit in the flow direction. Suitably such a plug part is mounted at or adjacent the outlet end of the flow conduit on radial spider-legs connecting the plug part to the sides of the flow conduit. Such an arrangement facilitates uniform flow of the fluid material around the plug part. Suitably such spider legs are located upstream in the flow direction from the outlet end of the flow conduit.

Preferably the outlet part incorporates an outlet conduit through which the fluid material flows with the outlet opening adjacent its end downstream in the flow direction. The closure part may fit into the upstream end of such an outlet conduit. Such an outlet conduit preferably tapers internally, preferably conically, narrowing toward the outlet opening, with the closure part having a correspondingly shaped surface profile to sealingly mate with the outlet conduit. Preferably the outlet opening tapers, preferably conically, narrowing in the direction upstream in the flow direction so that it is wider at its downstream end than further upstream. Therefore in a preferred embodiment the outlet conduit has a bi-frustroconical internal profile tapering inwardly from its upstream and downstream ends toward a narrow point between these two ends. It is found that such constructions advantageously provide better control of the flow of the fluid material and can avoid spraying of the fluid material as the outlet part returns to its closed position.

Suitably the outer profile of the neck part adjacent to the outlet end of the flow conduit corresponds closely to the internal profile of the outlet part so that when the outlet part is in its first position with the application opening closed by the closure part the neck part and the outlet part mate together to minimize fluid volume trapped between them.

In a preferred embodiment:

the applicator head of the invention is provided with connection means adapted to connect the applicator head to a squeeze tube of the fluid material, the neck part is a tubular member with the flow conduit following a straight line axis through the neck part, the skirt wall of the outlet part is a tight sliding fit on the outer surface of the neck part, and is reciprocally sideably moveable between a first position and a second position which are separated along the flow direction of the fluid material through the flow conduit, the external applicator surface comprises the external surface of an end wall across the skirt wall and from which the skirt wall descends and has a generally flat gently rounded external surface which extends across 70% or more of the widest cross sectional dimension of the outlet part and is substantially in a plane which is at an angle of 60°+/−10° to the flow direction and/or the elongate direction of a squeeze tube to which the applicator head is connected, the closure part comprises a plug part which extends from the outlet end of the conduit in the flow direction and is mounted at or adjacent the outlet end of the flow conduit on radial spider-legs connecting the plug part to the sides of the flow conduit.

Suitably the applicator head may be provided with a cover part which fits over the applicator head to protect it and to isolate it from the environment. Such a cover part may for example be a friction fit, a snap fit or a screw fit on the outlet part and/or on the neck part. As is common in the field the cover part may incorporate an opening spike to puncture a foil seal of a container of the fluid material such as a squeeze tube.

The parts of the applicator head are preferably made of plastics material such as polypropylene.

In a preferred embodiment the applicator head of this invention is provided connected to an elongate squeeze tube containing the fluid material and which is elongated in the flow direction.

The operation of the applicator head will now be described with reference to an applicator head connected to a squeeze tube of a fluid material by means of a screw thread connection of the inlet end of the flow conduit to a screw threaded nozzle of the squeeze tube.

The combination of applicator head and squeeze tube is provided to a user with the outlet part in its first position, with the application opening closed by the closure part and with a cover part fitting over the outlet part.

Any cover part present is removed from the applicator head. If necessary the applicator head is disconnected from the nozzle of the squeeze tube, any seal of the nozzle is removed or punctured, then the applicator head is replaced.

The outlet part is normally provided initially in its first position with the closure part closing the outlet opening. The outlet part is then moved along the neck part into its second, open, position disengaging the closure part from the outlet opening.

The squeeze tube may then be squeezed to extrude fluid material from the squeeze tube, through the flow conduit in the flow direction, through the outlet opening and onto the applicator surface. When sufficient fluid material has been extruded onto the applicator surface, the outlet part can be returned to its first position, causing the closure part to re-enter the outlet opening to close it. If the outer profile of the neck part adjacent to the outlet end of the flow conduit corresponds closely to the internal profile of the end wall these parts can mate together to expel fluid between them out through the outlet opening, thereby minimizing fluid material volume trapped between them.

The applicator surface can be brought into contact with the user's skin and used to spread the fluid material on the user's skin. When this has been completed the applicator surface may be wiped clean of fluid material and the cover replaced.

The invention will now be described by way of example only with reference to the accompanying drawings.

Figure 1:
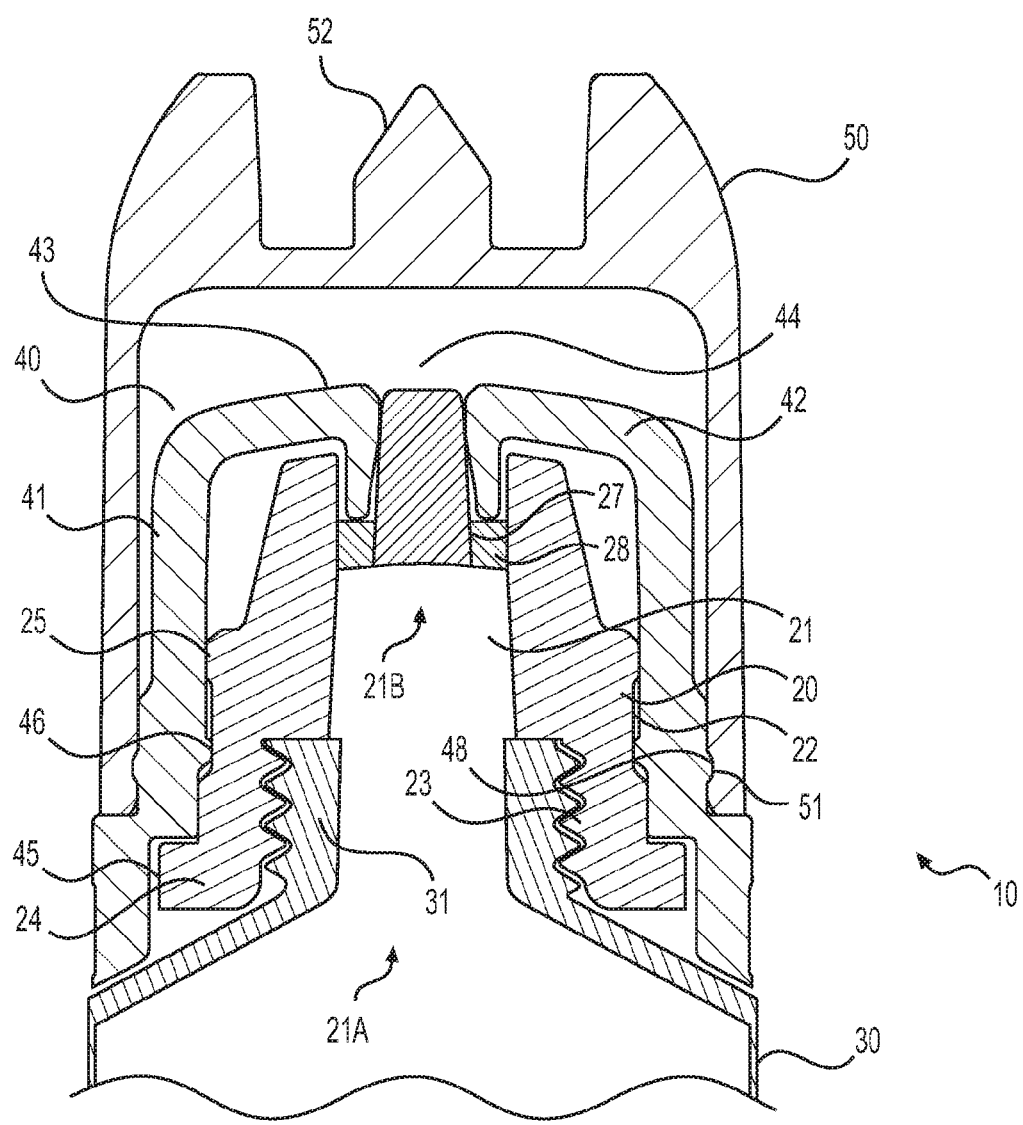
FIG. 1 shows a longitudinal section through an applicator head with the outlet part in the first position.

Referring to FIGS. 1-6, an applicator head for a fluid material is shown generally 10. The applicator head 10 comprises a neck part 20 having a flow conduit 21 through it for the flow of fluid material (not shown) in a flow direction shown by an arrow in FIG. 2 between an inlet end 21A of the conduit 21 and an outlet end 21B of the conduit 21. The neck part 20 is a tubular member with the flow conduit 21 following a straight line axis through the neck part 20. As can be seen more clearly from the perspective view FIG. 3 the neck part 20 has a cylindrical portion 22 on its outer surface. The inlet end 21A of the flow conduit 21 is provided with a screw thread 23 enabling connection to a squeeze tube 30 via a correspondingly screw threaded nozzle 31 of the squeeze tube 30.

Mounted externally on the neck part 20 is an outlet part 40 comprising a skirt wall 41 descending from an end wall 42. The skirt wall 41 is in the form of a generally cylindrical sleeve which is reciprocally sideably moveable on the cylindrical portion 22 of the neck part 20, between a first position as shown in FIG. 1 and a second position shown in FIG. 2 separated along the flow direction of the fluid material through the flow conduit 21, also being the elongate direction of the squeeze tube 30. The inner profile of the outlet part 40 corresponds closely to the outer profile of the neck part 20 so as to form a fluid material-tight sliding fit between them.

Figure 3:
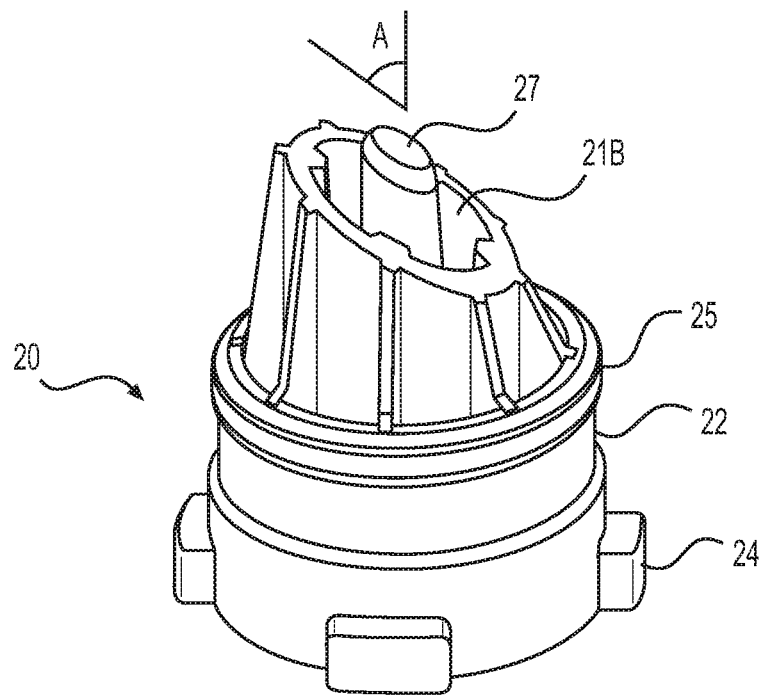
FIG. 3 shows a perspective external view of the neck part of an applicator head.
Figure 4:
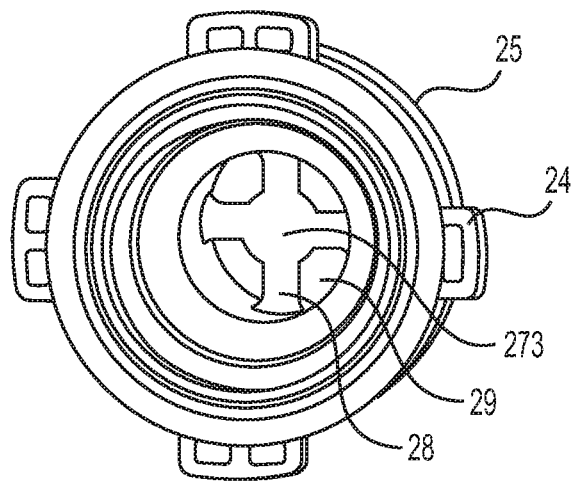
FIG. 4 shows a perspective internal view of the neck part of an applicator head.
Figure 5:
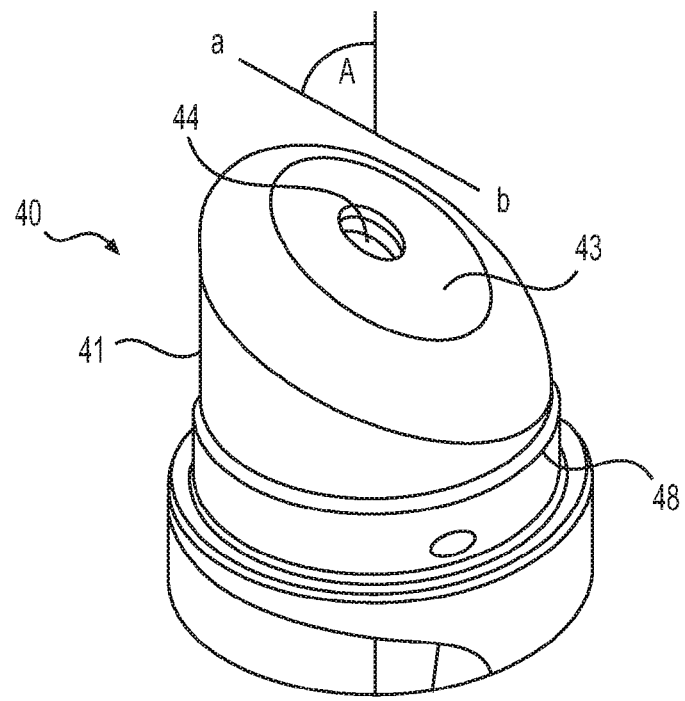
FIG. 5 shows a perspective external view of the outlet part of an applicator head.
Figure 6:
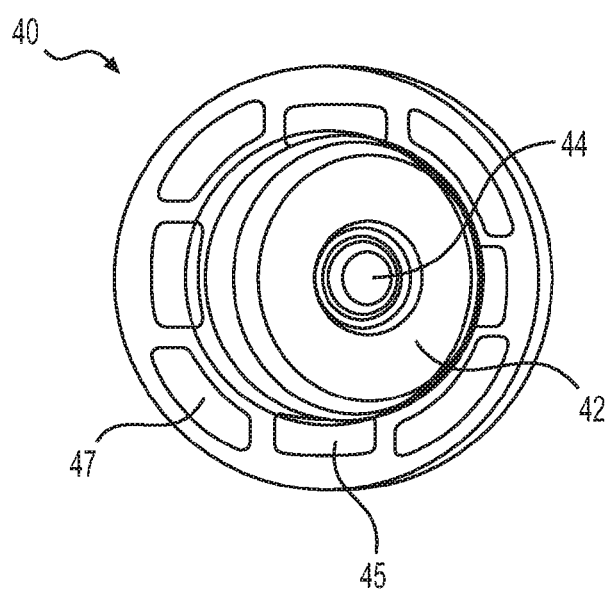
FIG. 6 shows a perspective internal view of the outlet part of an applicator head.

The outlet part 40 has an external applicator surface 43 being a generally flat but gently rounded part of the outer surface of the end wall 42, adapted to apply fluid material to a user's skin. The outlet part 40 has an outlet opening 44 through this end wall 42 through which fluid material may flow onto the applicator surface 43. FIG. 5 shows how the applicator surface 43 is an oval shape as viewed along the axis of the flow direction and extends across ca. 75% of the widest cross sectional dimension, cut across this axis, of the outlet part 40. As seen in FIG. 5 the applicator surface 43 is generally in a plane aligned in the direction a-b at an angle A to the elongate direction of the squeeze tube 30 (not shown in FIG. 5) of ca. 60°, and as seen in FIG. 3 the outer profile of the end of the neck part 20 adjacent to the outlet end 21B of the flow conduit 21 corresponds closely to the internal profile of the end wall 42 and is also generally in a plane at an angle A to the elongate direction of the squeeze tube 30 of ca. 60° so that the inner surface of the end wall 42 and neck part 20 mate together to minimize volume between them.

The neck part 20 and outlet part 40 also incorporate co-operating teeth 24 and slots 45 which maintain the rotational alignment of the outlet part 40 on the neck part 20 as the applicator part slides on the neck part 20. As can be seen more clearly in the perspective views in FIGS. 3, 4 and 6, and seen in cross section in FIGS. 1 and 2 the teeth 24 and the slots 45 are so shaped that the outlet part 40 will fit onto the neck part 20 in only one alignment in both the closed configuration of FIG. 1 and the open configuration of FIG. 2. Circumferentially between slots 45 are internal steps 47 which abut against teeth 24 to prevent relative rotation of the outlet part 40 on the neck part 20.

Figure 2:
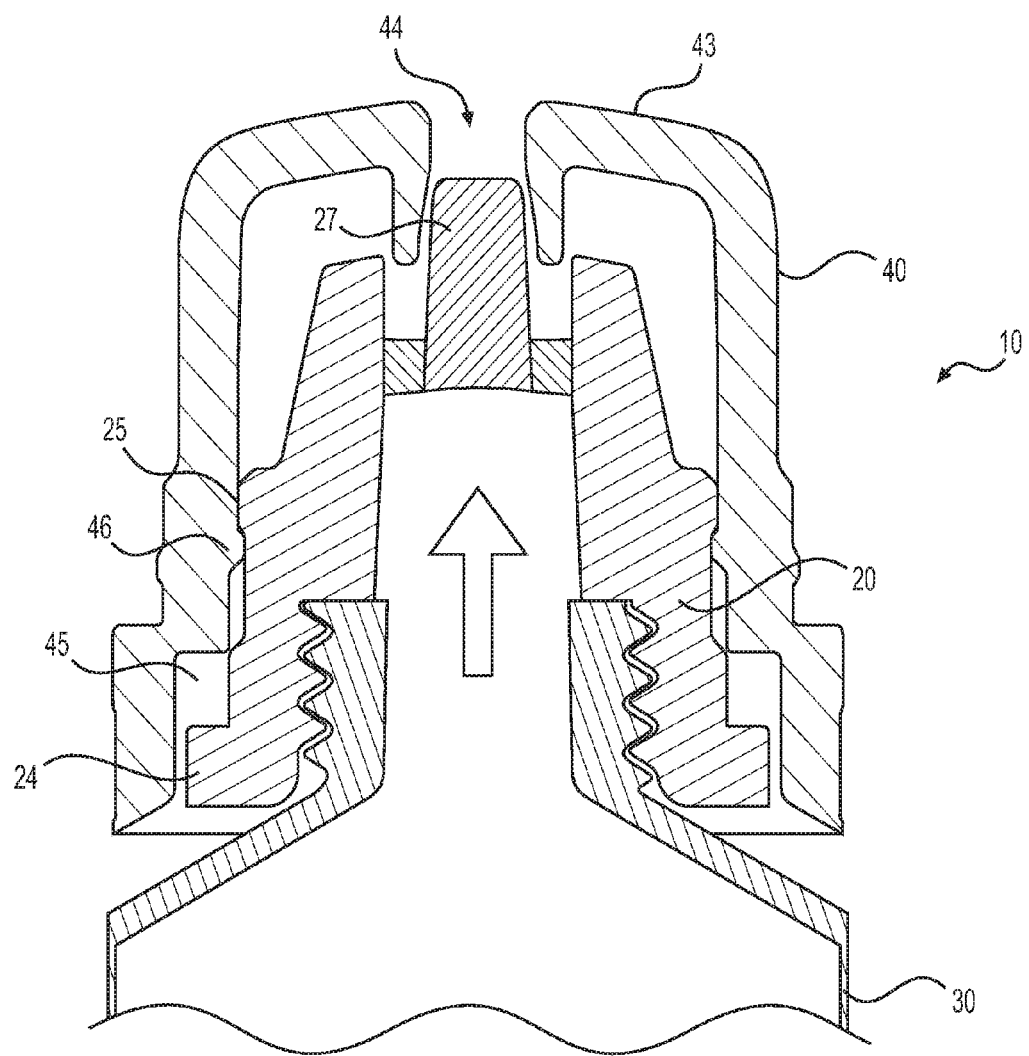
FIG. 2 shows a longitudinal section through an applicator head with the outlet part in the second position.

The neck part 20 and outlet part 40 have co-operating ridges respectively 25, 46 as shown in FIG. 1 which contact as shown in FIG. 2 to limit the distance the outlet part 40 can slide on the neck part 20 between the first and second positions. The engaging ridges 25, 46 snap-fit over each other to enable the outlet part 40 to be fitted over the neck part 20, and also prevent the outlet part 40 from being easily dislodged from the neck part 20, as shown in FIG. 2.

The neck part 20 also incorporates a closure part 27, being a closure plug with dimensions which correspond closely to those of the outlet opening 44. The closure part 27 extends from the outlet end 21B of the conduit 21 in the flow direction, and is mounted at the outlet end 21B on radial spider-legs 28 connecting the closure part 27 to the inner sides of the flow conduit 21 so that the fluid material can flow through the gaps 29 between the spider legs 28. As is best seen in FIG. 3 the spider legs 28 are located upstream in the flow direction from the outlet end 21B of the flow conduit 21.

Also mounted on the outer surface of the outlet part 40 is a removable cover 50 which is retained on the cover part 40 by a co-operating groove 51 and ridge 48. The cover 50 also incorporates a puncturing spike 52 which can be used to pierce any foil seal (not shown) over the nozzle of the squeeze tube 30.

The applicator head 10 is operated by first removing the cover 50. Then with the outlet part 40 and neck part 20 in the initial configuration as shown in FIG. 1 with the outlet part 40 in its first position and the outlet opening 44 closed by the plug part 27, the outlet part 40 is moved in the direction of the arrow in FIG. 2 into the second position as shown in FIG. 2, thereby disengaging the closure part 27 from the outlet opening 44 and thereby opening it to allow flow of fluid material.

It is seen that the ridges 25, 46 engage to limit the distance the outlet part 40 is able to move in this direction. The squeeze tube 30 may then be squeezed to extrude fluid material along the flow conduit 21 and out through the outlet opening 44 onto the applicator surface 43. When sufficient fluid material has been extruded onto the applicator surface 43 the fluid material on the applicator surface 43 can be applied to the user's skin, then the outlet part 40 can be returned to its first position as shown in FIG. 1.

After use, the cover 50 can be replaced on the applicator head 10 as shown in FIG. 1.

Referring to FIGS. 7-10 applicator heads having applicator surfaces of different shapes are shown. The applicator heads of FIGS. 7-10 are looking in a direction perpendicular to the elongate direction of a squeeze tube 30 to which they are attached.

Figure 7:
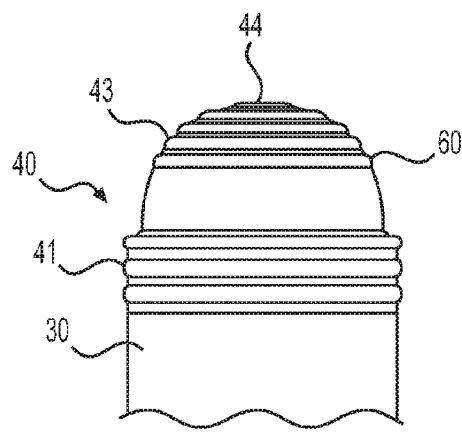
FIGS. 7-10 show orthogonal views of applicator heads having different forms of applicator surfaces.

FIG. 7 shows the outlet part 40 of an applicator head of the invention, which has a skirt wall 41 analogous to that of FIGS. 1-6. The external applicator surface 43 is of an external generally hemispherical shape, comprising the outer surface of both the end wall and skirt wall, with its spherical radius aligned with the elongate direction of the squeeze tube 30, this hemispherical shape merging with the skirt wall 41 in a smooth continuum. The applicator surface 43 is roughened by surface undulations in the form of plural ridges 60 which are generally circular in plan as viewed along the elongate direction of the squeeze tube 30 and are within each other, being concentrically arranged around an axis aligned with the elongate direction of the squeeze tube 30. The outlet opening 44 is located at the centre of these nested ridges 60.

Figure 8:
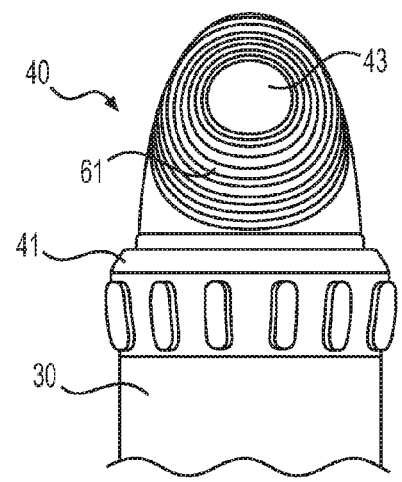
Figure 9:
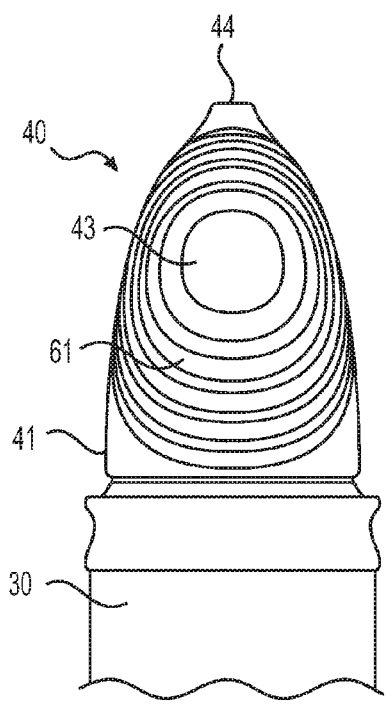

FIGS. 8 and 9 show the outlet part 40 of an applicator head of the invention, which has a skirt wall 41 analogous to that of FIGS. 1-6. The external applicator surface 43 is of an external generally ogival shape, comprising the outer surface of both the end wall and skirt wall. The applicator surface 43 of FIG. 8 is generally ovoid, that of FIG. 9 being more pointed, both having their rotation axis aligned with the elongate direction of the squeeze tube 30, and both facing transverse to the flow direction and/or the elongate direction of the squeeze tube 30. The applicator surface 43 is roughened by surface undulations in the form of plural ridges 61 which are generally oval in plan and are nested within each other. The outlet opening 44 is located at the rounded pointed end of the ogival-shaped outlet part 40 adjacent to the external applicator surface 43.

Figure 10:
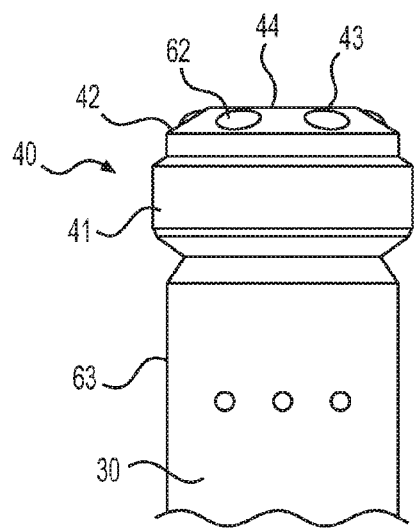

FIG. 10 shows the outlet part 40 of an applicator head of the invention, which has a skirt wall 41 analogous to that of FIGS. 1-6. The external applicator surface 43 comprises an external surface of an end wall 42 across the skirt wall 41 and from which the skirt wall 41 descends. The applicator surface 43 has a generally flat, gently rounded external surface and extends across a substantial proportion of the widest cross sectional dimension of the outlet part 40, and meets the skirt wall 41 with a rounded edge between them. The applicator surface 43 is substantially in a plane perpendicular to the elongate direction of the squeeze tube 30. In FIG. 10 The applicator surface 43 is roughened by surface undulations in the form of localized raised portions 62 of the external applicator surface 43, i.e. semi-spherical bumps on the applicator surface 43. In FIG. 10 the outlet opening 44 is a orifice through the external applicator surface 43, opening at its centre. The applicator head 10 of FIG. 10 has a sleeve part 63 which fits externally over a squeeze tube 30 to which it is connected, primarily for aesthetic reasons but also to facilitate a user's holding of the applicator head.

Internally the construction and operation of the applicator heads of FIGS. 7-10 are analogous to FIGS. 1-6.

Figure 11:
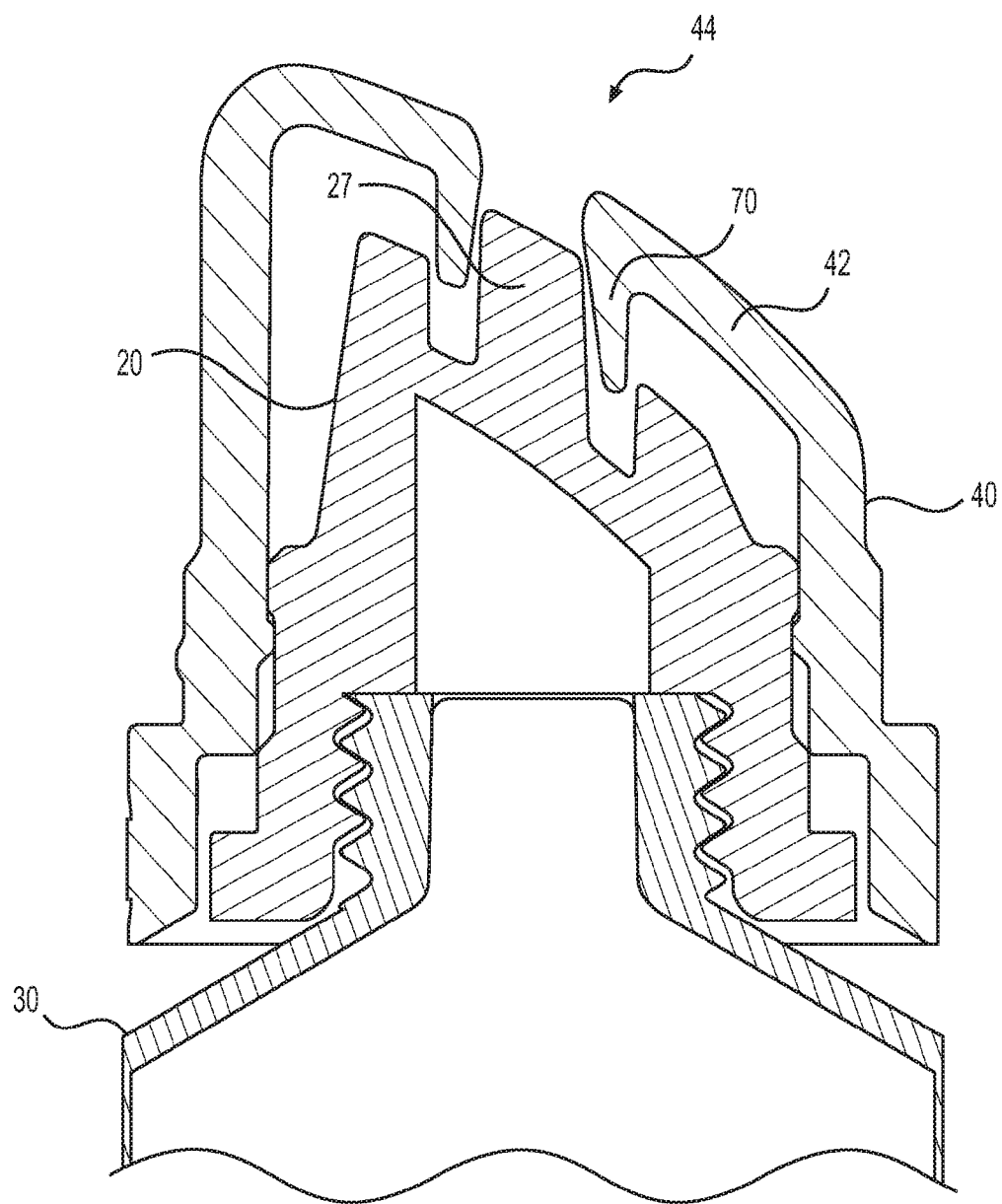
FIG. 11 shows an outlet part having an outlet conduit and a corresponding neck part.

FIG. 11 shows an applicator head with its outlet part 40 in the open configuration corresponding to FIG. 2. The outlet part 40 incorporates a tubular outlet conduit 70 extending inwardly within the outlet part 40 from the end wall 42, through which the fluid material flows with the outlet opening 44 adjacent its end downstream in the flow direction. The closure part 27 fits into the upstream end of the outlet conduit 70, which tapers conically internally, narrowing toward the outlet opening 44. The end of the closure part 27 has a correspondingly shaped surface profile so that in its closed configuration, corresponding to FIG. 1, the closure part mates sealingly with the outlet conduit 70. The outlet opening 44 also tapers conically, narrowing away from the applicator surface 43 in the direction upstream in the flow direction so that it is wider at its downstream end than further upstream. The combination of these two tapers results in the outlet conduit 40 having a bi-frustroconical internal profile tapering inwardly from its upstream and downstream ends toward a narrow point between these two ends.

The invention claimed is:

1. An applicator head for a fluid material comprising:
a neck part having a flow conduit for the flow of the fluid material in a flow direction between an inlet end of the conduit and an outlet end of the conduit and wherein the neck part is a tubular member with the flow conduit following a straight line axis through the neck part;
an outlet part comprising a skirt wall descending from an end wall and comprising a sleeve externally mounted on the neck part and being reciprocally slideably moveable on the neck part between a first position and a second position, the outlet part having an outlet opening through which fluid material may flow,
and wherein the neck part incorporates a closure part which when the outlet part is in the first position is engaged with the outlet opening to close flow of the fluid material from the flow conduit through the outlet opening, and when the outlet part is in the second position is disengaged from the outlet opening to allow flow of the fluid material from the flow conduit through the outlet opening;
and wherein the skirt wall of the outlet part is a tight sliding fit on the outer surface of the neck part, and is reciprocally slideably moveable between a first position and a second position which are separated along the flow direction of the fluid material through the flow conduit;
and wherein the applicator head is provided with connection means adapted to connect the applicator head to a squeeze tube of the fluid material;
and wherein the outlet part has an external applicator surface adapted to apply the fluid material to a user's skin and the outlet opening is an opening through the applicator surface characterised in that the outlet opening tapers, narrowing in the direction upstream in the flow direction so that said outlet opening is wider at said outlet opening's downstream end than further upstream;
and wherein the external applicator surface comprises an external surface of an end wall across the skirt wall and from which the skirt wall descends and has a generally flat gently rounded external surface which extends across 70% or more of the widest cross sectional dimension of the outlet part and is substantially in a plane which is at an angle of 60°+/−10° to the flow direction and/or the elongate direction of a squeeze tube to which the applicator head is connected; and
wherein the closure part comprises a plug part which extends from the outlet end of the conduit in the flow direction and is mounted at or adjacent the outlet end of the flow conduit on radial spider-legs connecting the plug part to the sides of the flow conduit.

2. The applicator head according to claim 1 characterised in that the applicator surface is in a plane perpendicular to the flow direction of the fluid material along the flow conduit.

3. The applicator head according to claim 2 characterised in that the applicator surface is in a plane which is at a non-perpendicular angle to the flow direction.

4. The applicator head according to claim 1 characterised in that the applicator surface is a generally hemispherical or ogival shaped part of the outer surface of the outlet part, with said applicator surface's rotation axis aligned with the flow direction.

5. The applicator head according to claim 4 characterised in that the applicator surface faces transverse to the flow direction.

6. The applicator head according to claim 1 characterized in that the external applicator surface is smooth.

7. The applicator head according to claim 1 characterised in that the external applicator surface is roughened with surface undulations.

8. The applicator head according to claim 7 characterised in that the surface undulations comprises one or plural surface ridges.

9. The applicator head according to claim 8 characterised in that plural surface ridges are generally circular or oval in plan and are nested within each other.

10. The applicator head according to claim 7 characterised in that the surface undulations comprises localized raised portions of the external applicator surface.

11. The applicator head according to claim 1 characterized in that the outlet part incorporates an outlet conduit through which the fluid material flows with the outlet opening adjacent to said outlet conduit end downstream in the flow direction and the outlet conduit tapers internally narrowing toward the outlet opening, with the closure part having a correspondingly shaped surface profile to sealingly mate with the outlet conduit.

12. The applicator head according to claim 1, which is connectable, or integrally connected to a container of the fluid material in a manner such that the fluid material content of the container is in flow communication with the flow conduit.

13. The applicator head according to claim 12, characterised in that the container of the fluid material is an elongate squeeze tube elongated in the flow direction.

* * * * *